United States Patent
Gagnon

(10) Patent No.: US 9,975,919 B2
(45) Date of Patent: May 22, 2018

(54) METHODS FOR REDUCING AGGREGATE CONTENT IN PROTEIN PREPARATIONS

(71) Applicant: AGENCY FOR SCIENCE, TECHNOLOGY AND RESEARCH, Connexis (SG)

(72) Inventor: Peter Stanley Gagnon, Centros (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 88 days.

(21) Appl. No.: 14/766,129

(22) PCT Filed: Feb. 5, 2014

(86) PCT No.: PCT/SG2014/000046
§ 371 (c)(1),
(2) Date: Aug. 5, 2015

(87) PCT Pub. No.: WO2014/123484
PCT Pub. Date: Aug. 14, 2014

(65) Prior Publication Data
US 2015/0368354 A1 Dec. 24, 2015

Related U.S. Application Data

(60) Provisional application No. 61/761,646, filed on Feb. 6, 2013.

(51) Int. Cl.
| | |
|---|---|
| *C07K 16/30* | (2006.01) |
| *B01D 15/36* | (2006.01) |
| *B01D 15/34* | (2006.01) |
| *C07K 16/00* | (2006.01) |
| *C07K 1/20* | (2006.01) |
| *C07K 1/14* | (2006.01) |
| *C07K 1/16* | (2006.01) |
| *B01D 15/32* | (2006.01) |
| *B01D 15/38* | (2006.01) |

(52) U.S. Cl.
CPC ............... *C07K 1/14* (2013.01); *B01D 15/34* (2013.01); *B01D 15/363* (2013.01); *C07K 1/165* (2013.01); *C07K 1/20* (2013.01); *C07K 16/00* (2013.01); *C07K 16/3015* (2013.01); *B01D 15/327* (2013.01); *B01D 15/3828* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,283,339 A * | 2/1994 | Arnold | ..................... | C07K 1/22 548/104 |
| 5,559,250 A | 9/1996 | Cook et al. | | |
| 2008/0177048 A1 * | 7/2008 | Gagnon | ............. | B01D 15/3847 530/413 |
| 2008/0193981 A1 | 8/2008 | Fahrner et al. | | |
| 2009/0143529 A1 * | 6/2009 | Hearn | ................ | B01D 15/3828 525/54.3 |
| 2009/0306342 A1 * | 12/2009 | Maeji | ............... | G01N 33/54393 530/344 |
| 2009/0318674 A1 * | 12/2009 | Gagnon | ................... | C07K 1/16 530/416 |

FOREIGN PATENT DOCUMENTS

| | | |
|---|---|---|
| JP | 2009053191 | 8/2008 |
| WO | WO 2011/140406 | 11/2011 |
| WO | 2012169970 A1 | 12/2012 |
| WO | WO 2013/180648 | 12/2013 |

OTHER PUBLICATIONS

Protein purification Profinity IMAC resins BIO-RAD bulletin 3193(Retrieved from http://www.bio-rad.com/webroot/web/pdf/lsr/literature/Bulletin_3193.pdf).*
Chelex 100 and 20 Chelating Ion Exchange Resin (2000,retrieved from http://www.bio-rad.com/webmaster/pdfs/9184_Chelex.PDF).*
Christensen et al., "Simple separation of DNA in antibody purification", Protein expression and purification 37, (2004), pp. 468-471.
Cordes et al., Precipitation of nucleic acids with poly(ethyleneimine), Biotechnol. Prog., (1990) 6, pp. 283-285.
Dissing et al., "Integrated removal of nucleic acids and recovery of LDH from homogenate of beef heart by affinity precipitation", vol. 7, Nos. 4-5, (1998), pp. 221-229.
Extended European Search Report dated Sep. 20, 2016 for Appln. No. 14748942.1.
Gagnon et al., "Chromatographic behavior of IgM:DNA complexes", Journal of Chromatography A, 1218, (2011), pp. 2405-2412.
Gagnon, "Dissociation of antibody-contaminant complexes with hydroxyapatite", Bioprocessing Journal, vol. 9, Issue 2, Winter 2010/2011, pp. 14-24.

(Continued)

*Primary Examiner* — Krishnan S Menon
*Assistant Examiner* — Ryan B Huang
(74) *Attorney, Agent, or Firm* — Pillsbury Winthrop Shaw Pittman LLP

(57) ABSTRACT

A method of reducing aggregate and product-contaminant complex content in a protein preparation including a desired protein includes (i) contacting the protein preparation with at least one solid surface comprising at least one surface-bound ligand capable of binding a metal, the surface-bound ligand being capable of binding a metal is initially substantially devoid of a metal, the operating conditions are selected to substantially prevent the binding of the desired protein to the at least one solid surface and (ii) separating the protein preparation from the surface-bound ligand, such that when more than one surface-bound ligand is present, each surface-bound ligand is independently either of the same net charge or charge neutral.

17 Claims, No Drawings

(56) References Cited

OTHER PUBLICATIONS

Gan et al., "Characterization and removal of aggregates formed by nonspecific interaction of IgM monoclonal antibodies with chromatin catabolites during cell culture production", Journal of Chromatography A 1291, (2013), pp. 33-40.
Glynn, "Process-scale precipitation of impurities in mammalian cell culture broth", 2009, pp. 309-324.
International Preliminary Report of Patentability dated Apr. 4, 2014 for Appl. No. PCT/SG2014/000046.
International Search Report dated Apr. 4, 2014 for Appl. No. PCT/SG2014/000046.
Kejnovsky et al., "DNA extraction by zinc", 1870-1871, Nucleic acids research, 1997, Vo. 25, No. 9.
Luhrs et al., "Evicting hitchhiker antigens from purified antibodies", Journal of Chromatography B 877, (2009), pp. 1543-1552.
Matsuzawa et al., Study on DNA precipitation with a cationic polymer PAC(poly aluminuim chloride), 2003, Nucleic acids research supplement No. 3, pp. 163-164.
Ma et al,, "Using precipitation by polyamines as an alternative to chromatographic separation in antibody purification processes", Journal of Chromatography B 878, (2010), pp. 798-806.
Mechetner et al., "The effects of hitchhiker antigens co-eluting with affinity-purified research antibodies", Journal of Chromatography B 879, (2011), pp. 2583-2594.
Ongkudon et al., "Analysis of selective metal-salt-induced endotoxin precipitation in plasmid DNA purification using improved limulus amoebocyte lysate assay and central composite design", Anal. Chem. 2011, 83, pp. 391-397.
Peram et al., "Monoclonal antibody purification using cationic polyelectrolytes: an alternative to column chromatography", Botechnol. Prog., 2010, vol. 26, No. 5, pp. 1322-1331.
Shukla et al., "Host cell protein clearance during protein a chromatography: development of an improved column wash step", Biotechnol. Prog. 2008, vol. 24, No. 5, pp. 1115-1121.
Akcasu et al., "5-Hydroxytryptamine in cerebrospinal fluid", vol. 187, 1960, p. 324-.
Legallais et al., "Strategies for the depyrogenation of contaminated immunoglobulin G solutions by histidine-immobilized hollow fiber membrane", Journal of Chromatography B., 1997, vol. 691, pp. 33-41.
"Protein Purification Profinity Tm IMAC Resins", Bio-Rad Laboratories Inc., Bulletin No. 3193., PDF document created 2005. Retrieved online Mar. 28, 2014 from http://www.bio-rad.com/webroot/web/pdf/lsr/literature /Bulletin_3193.pdf.
"Chelex 100 and Chelex 20 Chelating Ion Exchange Resin Instruction Manual", Bio-Rad Laboratories Inc., Bulletin No. LIT2000. PDF document created 1998. Retrieved online Mar. 28, 2014 from http://www.bio-rad.com/webroot/web/pdf/lsr/liturature/LIT200.pdf.
Bresolin, et al., "Adsorption of human serum proteins onto TREN-agarose: Purification of human IgG by negative chromatography," Journal of Chromatography B, 2009, 877, pp. 17-23.
Riordan, et al., "Salt Tolerant Membrane Adsorbers for Robust Impurity Clearance," Biotechnol Prog, 2009, 25(b), pp. 1695-1702.
Japanese Patent Office Action dated Nov. 21, 2017, in related Japanese patent application No. 2015-555967.

\* cited by examiner

METHODS FOR REDUCING AGGREGATE CONTENT IN PROTEIN PREPARATIONS

STATEMENT OF RELATED APPLICATIONS

This application claims priority to U.S. Provisional Application No. 61/761,646 filed Feb. 6, 2013, and is incorporated herein by reference in its entirety.

BACKGROUND

Embodiments disclosed herein relate to methods and materials for purification of proteins, including antibodies. In particular, embodiments relate to methods for reducing the content of aggregates and integration of these capabilities with other purification methods to achieve target purification levels of a protein.

It has been indicated that unnatural hetero-aggregates form spontaneously between host cell-derived contaminants and recombinant proteins produced by in vitro cell culture methods (Shukla et al., *Biotechnol. Progr.* (2008) 24:1115-1121; Luhrs et al., *J. Chromatogr. B* (2009) 877:1543-1552; Mechetner et al., *J. Chromatogr. B* (2011) 879:2583-2594; Gagnon et al., *J. Chromatogr. A*, (2011) 1218:2405-2412; Gagnon, *Bioprocessing J.* (2010) 9 (4):14-24). These hetero-aggregates may be considered unnatural in two respects: 1) constituent contaminants are often of non-human origin, secreted by living non-human host cells or released into the culture media when non-human host cells lyse upon death. In living humans, such non-human contaminants do not exist; and 2) constituent contaminants accumulate to high concentrations in comparison to human in vivo systems where dead cell constituents are quickly eliminated. Accordingly, recombinant products are exposed to high levels of strongly interactive contaminants at concentrations that typically do not occur in living systems. Meanwhile, high expression levels of recombinant proteins make them suitable substrates for non-specific associations with these non-human contaminants, favoring the formation of undesirable hetero-aggregates of diverse composition.

The specific source of contaminants that form stable associations with antibodies is not always known (see, for example, Shukla et al. supra). Some efforts have focused on DNA contaminants with little attention to the specific source of other possible contaminants (Gagnon et al. and Gagnon supra). Some efforts indicating an association of host contaminants with aggregates in antibody preparation have focused specifically on contaminants comprising chromatin catabolites (Luhrs et al., Mechetner et al. supra). In these examples, aggregation may be mediated directly through the immunospecificity of the antibody for chromatin catabolites such as histones and DNA. It has been indicated that chromatin catabolites are also capable of forming stable complexes with antibodies via non-specific interactions. Thus, monoclonal antibodies with known immunospecificities for antigens not including chromatin catabolites, can form highly stable aggregates of diverse descriptions with nucleosomes, histones, and DNA derived from the nuclei of dead host cells (Gan et al, *J. Chromatogr. A* 1291 (2013) 33-40). It has been particularly indicated that chromatin catabolites are highly represented in high molecular weight (HMW) aggregates. HMW aggregates are of particular concern because of their suspected involvement in promoting the formation of therapy-neutralizing antibodies. HMW aggregates are generally defined as aggregates of a size greater than small multiples of the antibody of interest.

Treating antibody preparations with agents that might be expected to dissociate hetero-aggregates has proven ineffective. For example, employing high concentrations of urea, salts, or combinations of the two does not substantially dissociate IgM-contaminant hetero-aggregates (Gagnon et al. supra). Many such aggregates have been proven stable even in strong chaotropes such as 4 M guanidine.

Conducting pre-elution washes of proteins bound to chromatography columns has supported some improvement. Protein A affinity chromatography with pre-elution washes of urea, alcohol, and surfactants has been indicated to reduce hetero-aggregate levels more effectively than without washes (Shukla et al. supra), as did pre-elution washes combining urea, salt, and EDTA with protein G affinity chromatography (Mechetner et al. supra). Anion exchange chromatography with a pre-elution wash of urea has been indicated to reduce hetero-aggregates more effectively than in the absence of a urea wash (Gagnon et al. supra). Cation exchange chromatography has also been indicated to reduce hetero-aggregates more effectively with a pre-elution EDTA wash than without the wash (Gagnon et al. supra). Finally, hydroxyapatite with pre-elution washes of urea and/or salt have also reduced hetero-aggregates more effectively than without such washes (Gagnon supra). Despite these observations, in general, the use of dissociating agents in pre-elution washes of antibodies bound to chromatography columns has been only moderately successful.

Organic multivalent cations have been indicated for the precipitation of acidic proteins (Farhner et al., U.S. Patent Application No. 20080193981; Ma et al., *J. Chromatogr. B* (2010) 878:798-806; Peram et al., *Biotechnol. Progr.*, (2010) 26:1322-1326; Glynn, in U. Gottschalk (ed.), *Process Scale Purification of Antibodies*, J. T. Wiley and Sons, (2009) Hoboken, 309-324), as well as for precipitation of DNA and endotoxins (Glynn supra; Cordes et al., Biotechnol. Progr., (1990) 6:283-285; Dissing et al., *Bioseparation*, (1999) 7 221:9-11) and inactivation of virus (Bernhardt, U.S. Pat. No. 5,559,250). Multivalent metal cations have also been indicated to remove DNA and endotoxin from some protein preparations (Akcasu et al., *Nature*, (1960) 187:323-324; Matsuzawa et al., *Nucl. Acids Res.*, (2003) 3 (3):163-164; Christensen et al., *Prot. Expr. Purif.*, (2004) 37:468-471; Kejnovsky et al., *Nucl. Acids Res.*, (1997) 25:1870-1871; Ongkudon et al., *Anal. Chem.*, (2011) 83 391:13-17).

Immobilized TREN (tris(2-aminoethyl)amine) is known and commercially available for the purpose of conducting immobilized metal affinity chromatography (IMAC), where the immobilized TREN is initially loaded with a metal ion, and biomolecules are captured by contact with the TREN-associated metal ion, then subsequently recovered by dissociating the target biomolecule from the metal ion. IMAC ligands other than TREN, such as iminodiacetic acid (IDA) and nitriloacetic acid (NTA), are also known and commercially available for the purpose of conducting IMAC, where the ligand is initially loaded with a metal ion, and biomolecules are captured by contact with the ligand-associated metal ion, then subsequently recovered by dissociating the target biomolecule from the metal ion.

SUMMARY

In some aspects, embodiments disclosed herein relate to methods of reducing aggregate and product-contaminant complex content in a protein preparation comprising a desired protein, the method comprising (i) contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the protein preparation from the at least one surface-bound ligand, wherein when more than one surface-bound ligand is present, each surface-bound ligand is independently either of the same net charge or charge neutral.

DETAILED DESCRIPTION

It has been surprisingly discovered that in certain embodiments methods employing a composition of matter comprising at least one solid surface comprising at least one surface-bound ligand capable of binding a metal, wherein the surface-bound ligand capable of binding a metal is initially substantially devoid of a metal, is effective in reducing the content of high molecular weight (HMW) aggregates and hetero-aggregates in protein preparations. In certain embodiments, the methods and compositions particularly reduce the content of aggregates that include chromatin remnants, such as nucleosomes, and/or histones, and/or DNA. In certain embodiments, methods disclosed herein have the additional ability to remove agents such as multivalent ions and antiviral compounds that may have been added to the protein preparation. It has been surprisingly discovered that in certain embodiments, the use of surface-bound metal affinity ligands reduces aggregate levels where soluble chelating agents do not. Without ascribing to any particular theory, this suggests that the effect may not be mediated through metals, but through a yet-unidentified chemical functionality embodied in ligands capable of binding metals; or alternatively or additionally through metals bound from the sample. A further unexpected discovery is the ability of some embodiments to remove protein fragments in addition to protein aggregates, which is especially difficult to understand since some embodiments remove both heavy and light chain contaminants from IgG preparations, in addition to removing aggregates.

In each embodiment disclosed herein, to achieve reduced aggregate levels the operating conditions are selected to substantially prevent the binding of the desired protein to each of the surface-bound ligands on all solid surface(s). In some embodiments, preventing binding of the desired protein may comprise adjusting a conductivity of the protein preparation. In some embodiments, preventing binding of the desired protein may comprise adjusting a salt concentration. Those skilled in the art will recognize that adjusting the salt concentration correlates with adjusting conductivity. In some embodiments, preventing binding of the desired protein may comprise the inclusion of a chaotropic salt. In some embodiments, preventing binding of the desired protein may comprise adjusting pH. In some embodiments, preventing binding may comprise including organic modifiers such as organic solvents, surfactants, chaotropes or other organic modifiers. In some embodiments, prevention of substantial binding of the desired protein to the surface-bound ligands may be mediated by compound approaches, such as a combination of pH and salt concentration, or a combination of salt concentration and an organic solvent, or a combination of salt concentration and a chaotrope, or any other combination. Thus, it will be appreciated by those skilled in the art that any combination of the aforementioned operational parameters may be adjusted to provide optimal operating conditions for a given desired protein.

In certain embodiments, another surprising feature of the methods disclosed herein is that aggregate levels are substantially reduced or eliminated despite the fact that the conductivity of the sample may be higher than necessary to avoid binding of the desired protein to the surface-bound ligands. In certain such embodiments, the conductivity of the sample is 5% greater than the level required to prevent substantial binding of the desired protein to the surface-bound ligands. In certain such embodiments, the conductivity of the sample is 10%, 20%, 50%, 100%, 200%, or 300% greater than the level required to prevent substantial binding of the desired protein to the surface-bound ligands.

In certain embodiments, another surprising feature of the methods disclosed herein is that the pH of the sample may be higher or lower than necessary to avoid binding of the desired protein to the surface-bound ligands. In one such embodiment involving negatively charged ligands, the pH may be 0.5 pH units higher than necessary to avoid binding of the desired protein to the surface-bound ligands. In one such embodiment, the pH may be 1 unit, or 2 units, or 3 units or more higher than necessary to prevent binding of the desired protein to the surface-bound ligands. In one such embodiment involving positively charged ligands, the pH may be 0.5 pH units lower than necessary to avoid binding of the desired protein to the surface-bound ligands. In one such embodiment, the pH may be 1 unit, or 2 units, or 3 units or more lower than necessary to prevent binding of the desired protein to the surface-bound ligands.

In certain embodiments, the methods disclosed herein can involve simultaneously contacting a sample containing a desired antibody with at least two species of surface-bound ligands, one bearing a surface bound ligand with an affinity for a metal or metal ion, and the other bearing other functionality without particularly having an affinity for metals or metal ions. Either ligand may embody chemical functionalities including, inter alia, hydrophobic, pi-pi bonding, hydrogen bonding, or electrostatic interactions. Where an additional ligand bears electrostatic properties, the net charge on the ligand is neutral or the same as the net charge on the metal affinity ligand. In certain embodiments, more than one species of ligand may provide different degrees of utility, potentially indicating that they individually favor interactions with different subsets of foreign substances. In certain embodiments, the different ligands may be distributed on different surfaces.

It has been surprisingly discovered that in certain embodiments aggregate levels in protein preparations can be dramatically reduced by the combined addition to such preparations of soluble multivalent ions of mixed chemical character and the subsequent addition of insoluble particles or other substrates of mixed chemical character. Experimental results indicate that this treatment permits dramatically greater reduction of high molecular weight (HMW) aggregate content and dissociation of hetero-aggregates than liquid phase treatments with salts and/or chaotropes, single-mechanism solid phase methods, or combinations of a solid phase method with an intended aggregate-dissociating wash. A valuable benefit of this approach is that one or more of the soluble agents are themselves removed from the protein preparation, yielding a substantially aggregate-free protein preparation, also substantially free of additives. This can surprisingly occur within a period of an hour or less even when the multivalent ions are present in extremely low amounts such as about 0.02 to about 0.025% and about 0.025 to about 0.5%, respectively. Experimental evidence further demonstrates that in certain embodiments, sample treatment in advance with the organic multivalent ions can enhance the results achieved.

In each embodiment disclosed herein, where soluble multivalent ions are included, the operating conditions are set to substantially prevent the precipitation of the desired protein. Adjusting the operating conditions to substantially prevent precipitation of the desired protein can be accomplished by, for example, adjusting the protein preparation conductivity, pH, or by including organic modifiers such as organic solvents, organic polymers, surfactants, and chaotropes. It will be appreciated by those skilled in the art that any combination of the aforementioned operational parameters may be adjusted to provide optimal operating conditions for a given desired protein.

Embodiments disclosed herein provide methods of reducing aggregate and product-contaminant complex content in a protein preparation comprising a desired protein, the method comprising (i) contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the protein preparation from the at least one surface-bound ligand; wherein when more than one surface-bound ligand is present, each surface-bound ligand is independently either of the same charge or charge neutral.

In some such embodiments, the surface-bound ligand capable of binding a metal provides further chemical functionality selected from the group consisting of electrostatic interactions, hydrophobic interactions, pi-pi interactions, hydrogen bonding, and combinations thereof.

In one or more of the preceding embodiments, the contacting step further comprises contacting the protein preparation with at least one surface-bound ligand that provides a chemical functionality that does not comprise binding a metal.

In one or more of the preceding embodiments, the at least one surface-bound ligand that provides a chemical functionality that does not comprise binding a metal is on the same solid surface as the at least one surface-bound ligand capable of binding a metal.

In one or more of the preceding embodiments, the at least one surface-bound ligand that provides a chemical functionality that does not comprise binding a metal is on a separate solid surface from the at least one surface-bound ligand capable of binding a metal.

In one or more of the preceding embodiments, the chemical functionality that does not comprise binding a metal provides a chemical functionality selected from the group consisting of electrostatic interactions, hydrophobic interactions, pi-pi binding, hydrogen bonding, and combinations thereof.

In one or more of the preceding embodiments, the net charge on the surface-bound ligand capable of binding a metal is positive.

In one or more of the preceding embodiments, the surface-bound ligand capable of binding a metal comprises one selected from the group consisting of tris(2-aminoethyl) amine (TREN), diethylenetriamine, triethylenetetramine, tetraethylenepentamine, polypropylenimine tetraamine, deferoxamine (desferrioxamine), histidine, histamine, arginine, lysine, polyhistidine, polyarginine, polylysine, and combinations thereof.

In one or more of the preceding embodiments, the net charge on the surface-bound ligand capable of binding a metal is negative.

In one or more of the preceding embodiments, the surface-bound ligand capable of binding a metal comprises one selected from the group consisting of iminodiacetic acid (2-(carboxymethylamino)acetic acid), ethylene glycol (aminoethylether) diacetic acid, diethyleaminetriaminepentaacetic acid, nitriloacetic acid (2,2',2''-nitrilotriacetic acid), aspartic acid, glutamic acid, polyaspartic acid, and combinations thereof.

In one or more of the preceding embodiments, methods may further comprise contacting the protein preparation with an organic additive to reduce the degree of aggregate contamination in the protein preparation.

In one or more of the preceding embodiments, the organic additive is a ureide.

In one or more of the preceding embodiments, the ureide is allantoin or urea.

In one or more of the preceding embodiments, allantoin is substantially soluble and present in a non-zero amount up to about 0.6%.

In one or more of the preceding embodiments, allantoin is substantially insoluble and present in a range of from about 1 to about 2%.

In one or more of the preceding embodiments, allantoin is substantially insoluble and present in a range of from about 1 to about 10%.

In one or more of the preceding embodiments, allantoin is substantially insoluble and present in a range of from about 1 to about 20%, or 30%, or 40%, or 50%.

In one or more of the preceding embodiments, urea is present in a range of from about 0.5 M to about 8 M In one or more of the preceding embodiments, urea is present in a range of from about 1 to about 4M.

In one or more of the preceding embodiments, urea is present in a range of from about 1 to about 2M.

In one or more of the preceding embodiments, the organic additive is an organic solvent.

In one or more of the preceding embodiments, the organic solvent comprises one selected from the group consisting of ethylene glycol, propylene glycol, dimethyl sulfoxide, ethanol, isopropanol, phenoxyethanol, and combinations thereof.

In one or more of the preceding embodiments, the organic solvent comprises one selected from the group consisting of ethylene glycol, propylene glycol, dimethyl sulfoxide, and combinations thereof, each independently present in a range of from about 1% to about 50% volume/volume, wherein a total aggregate amount of any combination is in a range from about 1% to about 50% volume/volume.

In one or more of the preceding embodiments, the organic solvent comprises one selected from the group consisting of ethylene glycol, propylene glycol, dimethyl sulfoxide and combinations thereof, each independently in a range of from about 1% to about 25% volume/volume, wherein a total aggregate amount of any combination is in a range from about 1% to about 25% volume/volume.

In one or more of the preceding embodiments, the organic solvent comprises one selected from the group consisting of dimethyl sulfoxide, ethanol, isopropanol, phenoxyethanol, and combinations thereof, each independently in a range of from about 0.05 to about 5% volume/volume, wherein a total aggregate amount of any combination is in a range from about 0.05% to about 5% volume/volume.

In one or more of the preceding embodiments, the organic additive comprises a surfactant.

In one or more of the preceding embodiments, methods may further comprise a nonionic or zwtterionic surfactant.

In one or more of the preceding embodiments, the nonionic or zwitterionic surfactant comprises one selected from the group consisting of Tween, Triton, Brij, CHAPS, CHAPSO, and octyl glucoside.

In one or more of the preceding embodiments, a surfactant concentration comprises a range of from about 0.001% to about 1%.

In one or more of the preceding embodiments, a surfactant concentration comprises a range of from about 0.01 to about 0.1%.

In one or more of the preceding embodiments, a conductivity of the protein preparation comprises a range of from about 0.1 mS/cm to about 40 mS/cm.

In one or more of the preceding embodiments, a conductivity of the protein preparation comprises a range from about 40 mS/cm to about 200 mS/cm.

In one or more of the preceding embodiments, a further solid surface does not substantially interact with the desired protein.

In one or more of the preceding embodiments, the operating conditions selected to substantially prevent the binding of the desired protein to the at least one solid surface comprises selecting a conductivity of the protein preparation sufficiently high to prevent substantial binding of the desired protein to each of the at least one surface-bound ligands.

In one or more of the preceding embodiments, the operating conditions selected to substantially prevent the binding of the desired protein to the at least one solid surface comprises selecting a conductivity of the protein preparation that is at least about 0.01%, about 0.1%, about 1%, or about 10% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 10% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 20% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 50% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 100% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 200% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 400% higher than the value required to prevent substantial binding of the desired protein to each of the at least one surface bound ligands.

In one or more of the preceding embodiments, the operating conditions are selected to substantially prevent the binding of the desired protein to the at least one solid surface comprises selecting a pH more than about 0.5 to about more than 4 units higher than necessary to prevent the binding of the desired protein.

In one or more of the preceding embodiments, the operating conditions are selected to substantially prevent the binding of the desired protein to the at least one solid surface comprises selecting a pH more than about 0.5 to about more than 4 units lower than necessary to prevent the binding of the desired protein.

In one or more of the preceding embodiments, a pH of the protein preparation comprises a range of from about 5 to about 9.

In one or more of the preceding embodiments, the at least one solid surface comprises a particle or composite of particles.

In one or more of the preceding embodiments, the at least one solid surface comprises a fiber or composite of fibers.

In one or more of the preceding embodiments, the at least one solid surface comprises a membrane or composite of membranes.

In one or more of the preceding embodiments, the at least one solid surface comprises a monolith or composite of monoliths.

In one or more of the preceding embodiments, different surface-bound ligands are present on structurally similar but distinct solid surfaces from the at least one solid surface comprising the at least one surface-bound ligand capable of binding a metal.

In one or more of the preceding embodiments, different surface-bound ligands are present on structurally distinct solid surfaces from the at least one solid surface comprising the at least one surface-bound ligand capable of binding a metal.

In one or more of the preceding embodiments, the protein preparation comprises a cell culture harvest.

In one or more of the preceding embodiments, the protein preparation comprises a clarified cell culture harvest.

In one or more of the preceding embodiments, the protein preparation comprises a recombinant protein.

In one or more of the preceding embodiments, the protein preparation comprises an antibody.

In one or more of the preceding embodiments, the protein preparation comprises greater than about 20% aggregates of the desired protein.

In one or more of the preceding embodiments, the protein preparation comprises greater than about 10% aggregates of the desired protein.

In one or more of the preceding embodiments, the protein preparation comprises greater than about 5% aggregates of the desired protein.

In one or more of the preceding embodiments, the protein preparation comprises greater than about 1% aggregates of the desired protein.

Kits may be provided for the convenient practice of any one of methods of the preceding embodiments.

In certain embodiments, methods are provided for reducing aggregate content of recombinant protein preparations, particularly including antibodies, clotting factors such as Factor VIII, and recombinant proteins. Without being bound to any specific theory, it has been unexpectedly discovered that aggregates are stabilized by interactions with foreign substances. Contacting an antibody preparation with multifunctional surfaces that have higher affinity for the foreign substances than the antibody have the effect of displacing the foreign substances, which can then be removed by simple removal of the multifunctional surfaces to which they are bound. In certain embodiments, aggregate levels are reduced substantially, and antibody recovery sometimes increases over the amount believed to be present, indicating the ability of the method to dissociate aggregates and restore the dissociated antibody to the purifiable product population. In certain embodiments, the method can also dissociate complexes of single antibodies with contaminants. In addition to producing antibody preparations with lower aggregate populations, in certain embodiments, the treated antibodies also exhibit lower host protein, DNA, endotoxin, and virus contamination.

In certain embodiments, the surfaces may include porous or non-porous particles dispersed throughout the protein preparation, or packed in a column, or initially dispersed and then packed in a column, or membranes, or monoliths, or fibers, or compound constructions.

In certain embodiments, aggregate removal can be enhanced by pre-treating the sample with soluble organic multivalent ions, alone or in combination with other agents, in which case the method has the additional utility of removing the organic multivalent ions, and potentially the other agents. Utility of the method may be otherwise enhanced by inclusion of antiviral agents, alone or in the presence of multivalent ions.

In some embodiments, there are provided methods of reducing aggregate and product-contaminant complex content in a protein preparation comprising a desired protein, the method comprising (i) contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the protein preparation from the at least one surface-bound ligand; wherein when more than one surface-bound ligand is present, each surface-bound ligand is independently either of the same charge or charge neutral.

In some embodiments, the surface-bound ligand capable of binding a metal provides further chemical functionality selected from the group consisting of electrostatic interactions, hydrophobic interactions, pi-pi interactions, hydrogen bonding, van der Waals interactions, and combinations thereof.

In one or more of the preceding embodiments, the contacting step further comprises contacting the protein preparation with at least one surface-bound ligand that provides a chemical functionality that does not comprise binding a metal.

In one or more of the preceding embodiments, the at least one surface-bound ligand that provides a chemical functionality that does not comprise binding a metal is on the same solid surface as the at least one surface-bound ligand capable of binding a metal.

In one or more of the preceding embodiments, the at least one surface-bound ligand that provides a chemical functionality that does not comprise binding a metal is on a separate solid surface from the at least one surface-bound ligand capable of binding a metal.

In one or more of the preceding embodiments, the chemical functionality that does not comprise binding a metal provides a chemical functionality selected from the group consisting of electrostatic interactions, hydrophobic interactions, pi-pi binding, hydrogen bonding, and combinations thereof.

In one or more of the preceding embodiments, the net charge on the surface-bound ligand capable of binding a metal is positive.

In one or more of the preceding embodiments, the surface-bound ligand capable of binding a metal comprises one selected from the group consisting of tris(2-aminoethyl)amine (TREN), diethylenetriamine, triethylenetetramine, tetraethylenepentamine, polypropylenimine tetraamine, deferoxamine (desferrioxamine), histidine, histamine, polyhistidine, and combinations thereof.

In one or more of the preceding embodiments, the net charge on the surface-bound ligand capable of binding a metal is negative.

In one or more of the preceding embodiments, the surface-bound ligand capable of binding a metal comprises one selected from the group consisting of iminodiacetic acid (2-(carboxymethylamino)acetic acid), ethylene glycol (aminoethylether) diacetic acid, diethyleaminetriaminepentaacetic acid, nitriloacetic acid (2,2',2''-nitrilotriacetic acid), aspartic acid, glutamic acid, polyaspartic acid, and combinations thereof.

In one or more of the preceding embodiments, methods may further comprise contacting the protein preparation with an organic additive to reduce the degree of aggregate contaminants in the protein preparation.

In one or more of the preceding embodiments, the organic additive is a ureide.

In one or more of the preceding embodiments, the ureide is allantoin or urea.

In one or more of the preceding embodiments, allantoin is substantially soluble and present in a non-zero amount up to about 0.6%.

In one or more of the preceding embodiments, allantoin is substantially insoluble and present in a range of from about 1 to about 2%.

In one or more of the preceding embodiments, allantoin is substantially insoluble and present in a range of from about 1 to about 10%.

In one or more of the preceding embodiments, allantoin is substantially insoluble and present in a range of from about 1 to about 20%.

In one or more of the preceding embodiments, urea is present in a range of from about 0.5 M to about 8 M In one or more of the preceding embodiments, urea is present in a range of from about 1 to about 4M.

In one or more of the preceding embodiments, urea is present in a range of from about 1 to about 2M.

In one or more of the preceding embodiments, the organic additive is an organic solvent.

In one or more of the preceding embodiments, the organic solvent comprises one selected from the group consisting of ethylene glycol, propylene glycol, dimethyl sulfoxide, ethanol, isopropanol, phenoxyethanol, and combinations thereof.

In one or more of the preceding embodiments, the organic solvent comprises one selected from the group consisting of ethylene glycol, propylene glycol, dimethyl sulfoxide, and combinations thereof, each independently in a range of from about 1% to about 50%.

In one or more of the preceding embodiments, the organic solvent comprises one selected from the group consisting of ethylene glycol, propylene glycol, dimethyl sulfoxide and combinations thereof, each independently in a range of from about 1% to about 25% and collectively in a range not greater than about 50%.

In one or more of the preceding embodiments, the organic solvent comprises one selected from the group consisting of dimethyl sulfoxide, ethanol, isopropanol, phenoxyethanol, and combinations thereof, each independently in a range of from about 0.05 to about 5% and collectively in a range not greater than about 50%.

In one or more of the preceding embodiments, the organic additive comprises a surfactant.

In one or more of the preceding embodiments, methods may comprise the use of a nonionic or zwtterionic surfactant.

In one or more of the preceding embodiments, the nonionic or zwitterionic surfactant comprises one selected from the group consisting of Tween, Triton, Brij, CHAPS, CHAPSO, and octyl glucoside.

In one or more of the preceding embodiments, a surfactant concentration comprises a range of from about 0.001% to about 1%.

In one or more of the preceding embodiments, a surfactant concentration comprises a range of from about 0.01 to about 0.1%.

In one or more of the preceding embodiments, a conductivity of the protein preparation comprises a range of from about 0.1 mS/cm to about 50 mS/cm.

In one or more of the preceding embodiments, a further solid surface does not substantially interact with the desired protein.

In one or more of the preceding embodiments, the operating conditions selected to substantially prevent the binding of the desired protein to the at least one solid surface comprises selecting a conductivity of the protein preparation sufficiently high to prevent substantial binding of the desired protein to each of the at least one surface-bound ligands.

In one or more of the preceding embodiments, the operating conditions selected to substantially prevent the binding of the desired protein to the at least one solid surface comprises selecting a conductivity of the protein preparation that is at least about 0.01%, or about 0.1%, or about 1%, or about 5%, higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 10% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 20% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 50% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 100% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 200% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a conductivity of the protein preparation that is at least 400% higher than the value required to prevent substantial binding of the desired protein to each of the at least one surface bound ligands.

In one or more of the preceding embodiments, the operating conditions selected to substantially prevent the binding of the desired protein to the at least one solid surface comprises selecting a pH.

In one or more of the preceding embodiments, the operating conditions selected to substantially prevent the binding of the desired protein to the at least one solid surface comprises providing an organic modifier.

In one or more of the preceding embodiments, a pH of the protein preparation comprises a range of from about 5 to about 9.

In one or more of the preceding embodiments, the at least one solid surface comprises a particle or composite of particles.

In one or more of the preceding embodiments, the at least one solid surface comprises a fiber or composite of fibers.

In one or more of the preceding embodiments, the at least one solid surface comprises a membrane or composite of membranes.

In one or more of the preceding embodiments, the at least one solid surface comprises a monolith or composite of monoliths.

In one or more of the preceding embodiments, different surface-bound ligands are present on structurally similar but distinct solid surfaces from the at least one solid surface comprising the at least one surface-bound ligand capable of binding a metal.

In one or more of the preceding embodiments, different surface-bound ligands are present on structurally distinct solid surfaces from the at least one solid surface comprising the at least one surface-bound ligand capable of binding a metal.

In one or more of the preceding embodiments, the protein preparation comprises a cell culture harvest.

In one or more of the preceding embodiments, the protein preparation comprises a clarified cell culture harvest.

In one or more the preceding embodiments, the protein preparation is partially purified.

In one or more of the preceding embodiments, the protein preparation comprises a recombinant protein.

In one or more of the preceding embodiments, the protein preparation comprises an antibody.

In one or more of the preceding embodiments, the protein preparation comprises an IgG antibody.

In one or more of the preceding embodiments, the protein preparation comprises a monoclonal IgG antibody.

In one or more of the preceding embodiments, the protein preparation comprises greater than about 20% aggregates of the desired protein.

In one or more of the preceding embodiments, the protein preparation comprises greater than about 10% aggregates of the desired protein.

In one or more of the preceding embodiments, the protein preparation comprises greater than about 5% aggregates of the desired protein.

In one or more of the preceding embodiments, the protein preparation comprises greater than about 1% aggregates of the desired protein.

In one or more of the preceding embodiments, the protein preparation comprises greater than about 0.1% aggregates of the desired protein.

In one or more of the preceding embodiments, the protein preparation comprises greater than about 0.01% aggregates of the desired protein.

In one or more of the preceding embodiments, after performing methods disclosed herein the remaining aggregate content may be less than about 5%, or less than about 2%, or less than about 1%.

A kit may be provided for the convenient practice of any one of the embodiments disclosed herein. Such a kit may provide all reagents and instructions for carrying out a purification of a desired protein.

In certain embodiments, methods are provided for reducing the aggregate content of a protein sample comprising a desired protein; certain methods include the steps of: (i) providing a first solid surface comprising at least one surface-bound ligand capable of binding a metal, wherein the surface-bound ligand capable of binding a metal is initially substantially devoid of a metal, (ii) providing a second solid surface comprising at least one surface-bound ligand lacking the capability of binding a metal, (iii) contacting the sample with the first and second solid surfaces, where the first and second solid surfaces are configured such that the sample may contact both surfaces simultaneously, wherein the operating conditions substantially prevent the binding of the desired protein to the first and second solid surfaces, and (iv) separating the protein sample containing the desired protein with a reduced aggregate content from the first and second solid surfaces.

In some embodiments, a third solid surface may be provided and the protein sample simultaneously contacted with the first, second and third solid surfaces. In some embodiments, a fourth solid surface may be provided and the protein sample simultaneously contacted with the first, second, third and fourth solid surfaces. Those skilled in the art will appreciate that any number of solid surfaces may be provided each bearing potentially different or variations of similar functionalities to enhance any number of interactions, such as electrostatic attraction, pi-pi bonding, hydrogen bonding, van Der Waals attraction, and the like, with the proviso that none of the solid surfaces possess opposite net charge to the metal affinity ligand.

In some such embodiments, the first and second solid surfaces are both electropositive. In other embodiments, the first and second solid surfaces are both electronegative. In still other embodiments, the first solid surface may be electropositive and the second solid surface is charge neutral. In yet still further embodiments, the first solid surface may be electronegative and the second solid surface charge neutral. In yet further embodiments, the first solid surface may be charge neutral and the second solid surface electropositive. In still further embodiments, the first solid surface may be charge neutral and the second solid surface electronegative. In yet still further embodiments both the first and second solid surfaces may be charge neutral.

In certain embodiments, an organic multivalent ion of mixed chemical character is combined with the sample prior to contacting the sample with the first and second solid surfaces. In certain embodiments, the first and second solid surfaces are combined prior to contacting the protein preparation. In certain embodiments, the sample is incubated with the organic multivalent ion of mixed chemical character for an appropriate period of time prior to contacting the sample with the first and second solid surfaces. In certain embodiments, the sample is incubated with the first and second solid surfaces for an appropriate period of time. In certain embodiments, the organic multivalent ion having mixed chemical character is removed from the sample in the step of separating the protein sample with a reduced aggregate content from the first and second solid surfaces to the extent that the organic multivalent ion having mixed chemical character is associated with a substrate of the first or second solid surfaces.

In certain embodiments, the first solid surface is particulate. In certain embodiments, the second solid surface is particulate. The particulate solid surfaces can each be provided as a plurality of particles. In certain embodiments, either or both of the particles of the first solid surface and the second solid surface can be non-porous or porous. Such porous particles can have average pore sizes which are large enough to permit entry of a protein in a protein preparation, or too small to permit entry of a protein in a protein preparation, or between about 10 nm and about 100 nm. In certain embodiments where the solid surfaces are particles, the particles may be sandwiched between porous membranes or monoliths. In certain embodiments, the particles may be sandwiched between woven or amorphous fibrous filters. In certain embodiments, the particles may be sandwiched between crystalline frits. In certain embodiments, the particles may be embedded in a reticular polymer network.

In certain embodiments, the conductivity of the sample is at a sufficiently high level to substantially avoid precipitation of the desired protein from the sample while contacting the first and second solid surfaces. In certain embodiments, the conductivity of the sample is greater than 20 mS/cm. In others, the sample is greater than 30 mS/cm, greater than about 40 mS/cm, or greater than about 100 mS/cm. In certain embodiments, the conductivity of the sample is at least 5%, 10%, 20%, 50%, 100% or 200% higher than the conductivity sufficient to substantially avoid precipitation of the desired protein from the sample while contacting the organic multivalent cation of mixed chemical character prior to the step of contacting the sample with the first and second solid surfaces.

In some embodiments, a top end of the conductivity range is higher than about three times physiological conductivity, but less than about four times physiological conductivity. Expressed as conductivity values where physiological conductivity is about 15 mS/cm, the methods disclosed herein may become more effective with increasing conductivity up to about 40 mS/cm, and then may decline thereafter until it becomes substantively less effective by the time it reaches about 60 mS/cm. One skilled in the art will appreciate that these values may shift upwards or downwards depending on the characteristics of the particular desired target protein.

In certain embodiments, the aggregates comprise homo-aggregates of the desired protein. In certain such embodiments, the presence of homo-aggregates of the desired protein is substantially eliminated. In certain embodiments, the aggregates comprise hetero-aggregates of the desired protein and a contaminant or multiple contaminants. In certain such embodiments, the hetero-aggregates are of substantially the same hydrodynamic size as the desired protein. In certain embodiments, the contaminant is a nucleic acid, nucleotide, endotoxin, metal ion, protein, lipid, or cell culture media component. In certain such embodiments, the presence of hetero-aggregates of the desired protein and a contaminant is substantially eliminated. In certain embodiments, the aggregates in the sample include both homo-aggregates and hetero-aggregates. In certain embodiments, the desired protein is an antibody or antibody fragment. In certain such embodiments, the sample is a protein preparation such as a cell culture harvest, a cell culture supernatant, an antibody-containing solution derived from a cell culture, or an antibody-containing solution from a previous stage of protein purification. In certain such embodiments, the protein preparation is an antibody-containing solution from a previous stage of protein purification. In certain such embodiments, the protein preparation is an eluate from a chromatography column.

In certain embodiments, the protein preparation may be unpurified, at an intermediate level of purity, or highly purified. In some embodiments, an intermediate level of purity of the sample may be in a range of from about 40% to about 90% purity. In some embodiments, the high level of purity of the sample may be in a range of from about 90% or greater.

In certain embodiments, the protein preparation is contacted with the first and second solid surfaces by flowing the preparation through the first and second solid surfaces.

In certain embodiments, the protein preparation is contacted with a first solid surface by suspending the solids in the protein preparation.

In certain embodiments, the protein preparation is contacted with a first and solid surface by suspending solids in the protein preparation.

In certain embodiments, the charge of the surface of the first or second solid surface is conferred through one or more kinds of complex chemical moieties that embody more than one chemical functionality, or through a combination of simple and complex chemical groups mixed on the surface, or a combination of surfaces of differing chemical composition. In certain embodiments, the charge of the surface of the first or second solid surface is conferred in part by a moiety from the group consisting of iminodiacetic acid, ethylene glycol(aminoethylether)diacetic acid, nitriloacetic acid, aspartic acid, glutamic acid, a carboxylic acid, sulfurous acid, sulfonate, or phosphoric acid. In certain embodiments, the charge of the surface of the first or second solid surface is conferred through one or more kinds of complex chemical groups that embody more than one chemical functionality, or through a combination of simple and complex chemical groups mixed on the surface, or a combination of surfaces of differing chemical composition. In certain such embodiments, the charge of the surface of the first or second solid surface is conferred in part by a moiety selected from the group consisting of tris(2-aminoethyl)amine, diethylenetriamine, triethylenetetramine, tetraethylenepentamine, polypropylenimine tetramine, PAMAM dendrimer (ethylenediamine core), deferoxamine, a primary amino group, a secondary amino group, a tertiary amino group, and a quaternary amino group. In certain embodiments, the charge of the surface of the first or second solid surface is conferred in part by iminodiacetic acid and the electropositivity of the surface of the second component is conferred in part by a moiety from the group consisting of tris(2-aminoethyl) amine (TREN). In certain embodiments, the first solid surface has a surface-bound chemical moiety possessing metal affinity functionality and the second solid surface is a second substrate having a charged surface that is the same as the first solid surface. In certain embodiments, the second solid surface is a second substrate having a charged surface and the first solid surface includes a surface-bound chemical moiety possessing metal affinity functionality. In certain such embodiments, at least one of the substrates has one or more chemical moieties in addition to the surface-bound chemical moiety possessing metal affinity functionality wherein such additional chemical moieties enhance the capacity of one or more of the components to participate in hydrogen bonding, hydrophobic interactions, or pi-pi binding with a protein of the protein preparation. In certain embodiments, the surface-bound chemical moiety possessing metal affinity functionality is a multidentate metal chelating moiety.

In certain embodiments, the protein sample is treated with an organic multivalent cation of mixed chemical character before exposure to the surfaces of the first and second components. Such organic multivalent cations may include ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), methylene blue, phenosafranin, phenoxazine, phenothiazine, acriflavine (3,6-diamino-10-methylacridinium, chloride and 3,6-acridineidiamine), polyethyleneimine, chlorhexidine, or a poly-amino acid. In certain embodiments, the organic multivalent cation of mixed chemical character is ethacridine, methylene blue, polyethylenimine or chlorhexidine or a salt thereof. In certain embodiments, the organic multivalent cation of mixed chemical character is ethacridine or methylene blue, or cetyltrimethylammonium, or a salt thereof. In certain such embodiments, the organic multivalent cation of mixed chemical character is present in an amount between approximately 0.01% and approximately 0.05%. In certain embodiments, the organic multivalent cation of mixed chemical character is present in an amount less than approximately 0.01%. In certain embodiments, the organic multivalent cation of mixed chemical character is present in an amount less than approximately 0.005%. In certain embodiments, the organic multivalent cation of mixed chemical character is present M an amount less than approximately 0.001%. In certain embodiments, the organic multivalent cation of mixed chemical character is present in an amount between approximately 0.020 and approximately 0.025%.

In certain embodiments, the sample is treated with one or more organic multivalent cations such as polyethyleneimine, polyallylamine, ethacridine, methylene blue, or chlorhexidine, or cetyl trimethyl ammonium, and salts thereof prior to the step of contacting the sample with the first and second components. In certain such embodiments, the organic multivalent cations used to treat the sample prior to the step of contacting the sample with the first and second components are provided in a concentration of less than 1%. In certain embodiments, the organic multivalent cations used to treat the sample prior to the step of contacting the sample with the first and second components are provided in a concentration between approximately 0.01% and approximately 0.05%, or in a concentration less than approximately 0.01%, or in a concentration less than approximately 0.005%, or in a concentration less than approximately 0.001%, or in a concentration between approximately 0.020 and approximately 0.025%.

In certain embodiments, the sample is treated with one or more organic multivalent anions such as a fatty acid or a polyanion, where examples of the former may include heptanoic acid, octanoic acid, octenoic acid, nonanoic acid, nonenoic acid, and decanoic acid at concentrations ranging from 0.05% to 5%; and examples of the latter may include polyaspartate, polyglutamate, or other negatively charged polymers, or negatively charged heteropolymers synthesized from differing subunits.

In certain embodiments, the protein sample is additionally contacted with a soluble organic modulator selected from the group consisting of nonionic organic polymers, organic solvents, surfactants, and ureides, where such step of contacting the sample with soluble organic modulators occurs prior to the step of contacting the sample with the first and second components.

In certain embodiments, the sample is additionally contacted with an antiviral agent, where such step of contacting the sample with an antiviral agent occurs prior to the step of contacting the sample with the first and second components. In certain such embodiments, the antiviral agent is a non-multivalent organic cation such as benzalkonium chloride, methylene blue, chlorhexidine, or tri (n-butyl) phosphate. In certain such embodiments, the antiviral agent is present in an amount less than approximately 1% (w/v), or in an amount less than approximately 0.1% (w/v), or in an amount less than approximately 0.01% (w/v), or in an amount less than approximately 0.001% (w/v).

In certain embodiments, methods provide the additional steps of contacting the sample with a ureide in an amount sufficient for the ureide to be supersaturated in the protein preparation, and separating the supernatant containing the desired protein from the portion of the protein preparation, where such step of contacting the sample with such ureide occurs prior to the step of contacting the sample with the first and second solid surfaces. In certain such embodiments, the ureide is urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, imidazolidinyl urea, diimidazolidinyl urea, or a purine. In certain such embodiments, the ureide is allantoin. In others, the ureide is uric acid. In certain embodiments, the allantoin is present in an amount greater than 0.5% (w/v), or in an amount greater than approximately 1% (w/v). In certain embodiments, the uric acid is present in an amount greater than 0.0025% (w/v), or in an amount greater than approximately 0.01% (w/v), or in an amount greater than approximately 0.1% (w/v), or in an amount greater than approximately 1% (w/v).

In certain embodiments, the organic modulator is a nonionic organic polymer selected from the group consisting of polyethylene glycol, polypropylene glycol and polybutylene glycol. In certain embodiments; the nonionic organic polymer has an average molecular weight of approximately 500 D or less. In certain embodiments, the organic modulator is an organic solvent such as ethylene glycol, propylene glycol, butylene glycol, dimethylsulfoxide, ethanol, or phenoxyethanol. In certain embodiments, the organic modulator is provided at a concentration of approximately 1% (w/v) or greater. In certain embodiments, the organic modulator is a surfactant selected from the group consisting of Tween, triton, CHAPS, CHAPSO and octyl glucoside. In certain such embodiments, the surfactant is provided at a concentration of approximately 1% (w/v) or less, or at a concentration of approximately 0.1% (w/v) or less. In certain embodiments, the organic modulator is a ureide provided in a subsaturating amount. In certain such embodiments, the ureide is selected from the group consisting of urea, hydantoin, and allantoin.

In certain embodiments, there are provided kits for the convenient practice of method embodiments including some or all of the materials needed for performance of the methods, generally in amounts and concentrations convenient for the performance of methods disclosed herein.

Terms are defined so that embodiments may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homoaggregates" refers to a stable association of two or more antibody molecules; "Hetero-aggregates" refers to a stable association of one or more antibody molecules with one or more non-antibody molecules. The non-antibody component may consist of one more entities from the group consisting of a nucleotide, an endotoxin, a metal ion, a protein, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, $F(ab')_2$, Fv, scFv, Fd, dAb, Fc and other compositions, whether or not they retain antigen-binding function.

"Electropositive surface" refers to a surface of a substrate or solid material which is dominated by positive charge. Electropositivity of a surface may be conferred by chemical groups including but not limited to weak anion exchange groups, like amino, ethylene diamino, diethylaminoethyl, polyallylamine, polyethyleneimine, strong anion exchange groups, such as quaternary amino groups, combined weak-strong exchangers, such as polylysine, polyarginine, or Tris(2-aminoethyl)amine, diethylenetriamine, triethylenetramine, tetraethylenepentamine, polypropylenimine tetraamine, PAMAM dendrimer (ethylenediamine core), deferoxamine or any combinations of the foregoing. Secondary functionalities that create a mixed chemical character on a positively charged surface may consist of negatively or positively charged groups, hydrophobic groups, pi-pi bonding groups, hydrogen-bonding groups, or metal-chelation groups. The secondary functionalities may exist on electropositive surfaces as an inadvertent byproduct of the manufacturing materials or process by which the particles are synthesized, or they may be present by deliberate design. The concentration of secondary functionalities may range from less than 1 milliequivalent per mL of particles, to more than 100 milliequivalents per mL.

"Electronegative surface" refers to a surface of a substrate or solid material which is dominated by negative charge. Electronegativity of a surface may be conferred by chemical groups including but not limited to so called weak cation exchangers, such as carboxyl, aminocarboxyl (iminodiacetic or nitriloacetic), or phosphoryl or strong exchangers such as sulfo, or sulfate moieties, SO3⁻. Secondary functionalities that create a mixed chemical character on a negatively charged surface may consist of negatively or positively charged groups, hydrophobic groups, pi-pi bonding groups, hydrogen-bonding groups, or metal-chelation groups. The secondary functionalities may exist on electronegative surfaces as an inadvertent byproduct of the manufacturing process by which the particles are synthesized, or they may be present by deliberate design. The concentration of secondary functionalities may range, from less than 1 milliequivalent per mL of particles, to more than 100 milliequivalents per mL.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Ligand" or "surface-bound ligand" refers an assemblage consisting of one or more chemical moieties or functionalities that bind to some other chemical entity. In the present embodiments, a ligand is immobilized on a surface with the intent of binding sample (protein preparation) components that contribute to formation or stabilization of aggregate. A ligand may be fairly simple in composition, such as a negative charge, positive charge, or hydrophobic group, or it may be of more complex construction, including two or more distinct components that endow the ligand with the ability to bind chemical entities through interactions that none of the components are individually capable of. In addition, a given ligand may embody abilities to interact with other entities through mechanisms other than its primary or dominant mechanism. For example, the metal affinity ligand iminodiacetic acid contains two carboxyl groups that are negatively charged under most operating conditions, and a nitrogen group that can be positively charged at low pH. In addition to embodying metal affinity, it can also interact with other chemical entities by electrostatic interactions and hydrogen bonding. The metal affinity ligand TREN, when immobilized on a surface, includes 2 primary amines, 1 secondary amine, and 1 tertiary amine. TREN as a whole can form a strong association with a metal dissolved in aqueous solution, while the individual amines can participate in electrostatic and/or hydrogen bonds.

"Metal affinity functionality" refers to the capacity of a chemical moiety, which may be immobilized on a surface, to bind metal ions, such as in a 1:1 fashion. Such moieties may have the capacity to form coordination bonds with a metal ion and certain such moieties may be bidentate or multidentate in character. Nonlimiting examples of electronegative moieties with this capability include iminodiacetic acid (2-(carboxymethylamino) acetic acid) and nitriloacetic acid (2,2',2"-Nitrilotriacetic acid). An example of an electropositive compound with this capability includes but is not limited to Tris(2-aminoethyl)amine or diethylenetriamine, triethylenetetramine, tetraethylenepentamine, polypropylenimine tetraamine, and deferoxamine.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the methods disclosed herein include but are not limited to polyethylene glycol (PEG), polypropylene glycol, and polyvinylpyrrolidone (PVP). PEG has a structural formula HO—($CH_2$—$CH_2$—O)$_n$—H. Examples include, but are not limited to compositions with an average polymer molecular weight ranging from less than 100 to more than 1000 daltons.

"Organic multivalent ion" refers to an organic molecule, ion or salt of natural or synthetic origin that embodies at least one charge and at least one additional chemical functionality, thus rendering it multivalent. In certain embodiments, an organic multivalent ion the at least one additional chemical functionality is an additional charge such that the organic multivalent cation bears two or more like or differing charges. The organic multivalent ion may bear a net positive, net negative, or net neutral charge. Where the organic multivalent ion is net positive it may be provided together with anions such as chlorides, bromides, sulfates, organic acids, lactates, gluconates, and any other anion not incompatible with the method. In certain embodiments certain of the positive charges of the organic multivalent ion are supplied by amine, imine or other nitrogen moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in certain embodiments include but are not limited to the diamino acids, di-, tri-, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris (2-aminoethyl)amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates, such as cetyl trimethyl ammonium bromide.) Where the organic multivalent ion is net negative it may be provided together with cations such as sodium or potassium, or any other cation not incompatible with the method. In certain embodiments certain of the negative charges of the organic multivalent ion are supplied by carboxyl, phospho, or sulfo moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in certain embodiments include but are not limited to the fatty acids such as heptanoic acid, octanoic acid, nonanoic acid, decanoic acid, anionic polymers, and salts thereof (e.g. chlorides, bromides, sulfates, lactates, gluconates). Organic multivalent ions may include of a particular net charge may include oppositely charged moieties. For example, an organic multivalent ion with a net positive charge may include one or more negative charges, or a species with a net negative charge may include one or more positive charges.

"Organic solvent" refers to naturally occurring or synthetic organic compound existing in a liquid state. Examples suitable to practice the methods disclosed herein include but are not limited to ethylene glycol, propylene glycol, dimethyl sulfoxide, ethanol, and phenoxyethanol.

"Physiological conductivity" refers to a value of about 15 mS/cm, which corresponds roughly to a sodium chloride concentration of about 150 mM. Different salts and ions of different composition may individually confer different levels of conductivity than sodium chloride. In original biological solutions, the conductivity value may be conferred by salts of multiple species. In experimental solutions, conductivity may be conferred by a single species of salt, or dominantly by a single species of salt. Use of conductivity as a functional measure of overall salt concentration thereby provides an unambiguous expression of equivalence between solutions of different composition.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones. "Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Substrate" or "Solid material" refers to an insoluble organic solid that may be particulate, crystalline, polymeric, fibrous, porous-hollow fibrous, monolithic, membranaceous, in nature. It may consist of non-porous or porous particles, a porous membrane, a porous filter, or a porous monolith. If particulate, the particles may be roughly spherical or not, and may be of sizes ranging from less than 100 nm to more than 100 microns. The average pore size of porous particles may range less than 10 nm (microporous) to more than 100 nm (macroporous). The average pore size in membranes may range from less than 100 nm to more than 1 micron. The average channel size in membranes or monoliths may range from less than 1 micron to more than 10 microns. The solid material may further consist of compound constructions, for example in which particles are embedded in a reticular matrix, sandwiched between membranes, or both.

"Supersaturated ureide" refers to a solution containing an amount of ureide in excess of its maximum solubility under the conditions prevailing in a particular protein preparation. In certain embodiments, methods provide a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl)dimethylammonio]-2-hydroxy-1-propanesulfonate), and octyl glucoside (e.g., (2R,3S,4S,5R,6R)-2-(hydroxymethyl)-6-octoxyoxane-3,4, 5-triol).

"Ureide" refers to a cyclic or acyclic organic molecule of natural or synthetic origin that comprises one or more urea moieties or derivatives thereof. In certain embodiments, methods provide ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, methods provide organic molecules of the formula R—CO—NH—CO—NH$_2$ or R—CO—NH—CO—NH—CO—R' or R'R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

The solid materials used to practice the methods disclosed herein may include insoluble particles of natural or synthetic origin, such as but not limited to porous microparticles commonly employed for practicing chromatography. Such particles may embody large pores that permit the diffusive entry of proteins, such as but not limited to antibodies; or they may embody small pores that allow the diffusive entry of small chemical species such as salts, sugars, and heteroaggregate-dissociating agents, but are too small to permit the entry of proteins such as antibodies.

The solid materials may alternatively include non-porous particles, membranes or monoliths, fibers including porous-walled hollow fibers, porous membranes, and/or compound constructions employing combinations of the above elements.

The particles of mixed chemical character used to practice the certain embodiments particularly include insoluble organic particles. Such particles may be non-porous or porous. If porous, they may embody large pores that permit the diffusive entry of proteins, such as but not limited to antibodies; or they may embody small pores that allow the diffusive entry of small chemical species such as salts, sugars, and hetero-aggregate-dissociating agents, but are too small to permit the entry of proteins such as antibodies. The mixture of chemical characteristics embodied by such particles may include an electronegative functionality to scavenge soluble multivalent cation agents of mixed chemical character, and may further include one or more chemical functionalities that may enhance their ability to reduce aggregate content and/or facilitate the scavenging of soluble agents, including but not limited to electropositivity, hydrogen bonding, hydrophobic interactions, pi-pi bonding, and metal coordination. Where a given ligand comprises more than one kind of charge, it is understood that the charges are either balanced, creating an electro-neutral condition, or the charge is dominated by one or the other charge so that its net charge is the same as solid surface with the metal affinity functionality.

Electropositive groups may include so-called strong anion exchange groups and/or so-called weak anion exchange groups. Electropositive groups of mixed strong-weak anion exchange may be beneficial for their ability to achieve a higher degree of aggregate reduction. A non-limiting example of such a mixed weak-strong anion exchange group with elevated ability to remove aggregates is Tris(2-aminoethyl)amine (TREN). Mixed chemical character may reside in a single complex chemical group, in separate chemical groups of distinct character on a single type of surface, on distinct surfaces, or any combination of the foregoing. Weak ion exchange groups, including in combination with strong ion exchange groups, may also be useful for their elevated ability to form hydrogen bonds in comparison to strong ion exchange groups.

Electronegative groups may include so-called strong cation exchange groups, so-called weak cation exchange groups, or electronegative groups of mixed strong-weak cation exchange groups. Such groups may be useful for their ability to participate in coordination interactions with dissolved metal ions, producing the desirable result of removing contaminating metal ions from the applied biological sample. Non-limiting examples of cation exchange groups include sulfo, carboxy, phosphoryl, iminodiacetic (IDA), and nitriloacetic acid (NTA) groups. Weak ion exchange groups, including in combination with strong ion exchange groups, may also be useful for their elevated ability to form hydrogen bonds in comparison to strong ion exchange groups.

In certain embodiments, the surfaces of the electropositive or electronegative materials may also embody hydrophobic groups of an aliphatic and/or or aromatic character, where the latter may be useful because of their ability to participate in so-called pi-pi bonding. Mixed chemical character may reside in a single complex chemical group, in separate chemical groups of distinct character on a single type of surface, on distinct surfaces, or any combination of the foregoing.

Chemical functionalities of differing individual character may be employed in various ratios customized to the needs of a particular sample composition. For example, combinations intended for treatment of clarified cell culture supernatant may include an excess of electropositive surfaces, while combinations intended for treatment of supernatant already treated with electropositive hetero-aggregate-dissociating agents such as ethacridine or methylene blue may include an excess of electronegative surfaces.

Soluble multivalent cations of mixed chemical character used to practice certain embodiments may include organic molecules with at least one positive charge and additional features that confer a mixed chemical character such as moieties providing the ability to participate in hydrogen bonding, hydrophobic interactions, pi-pi bonding, metal coordination, and intercalation. Examples of multivalent cations embodying these characteristics include polyethyleneimine, ethacridine, methylene blue, cetyl trimethylammonium bromide, chlorhexidine, and numerous others. Such agents may be applied at concentrations ranging from 0.001% to 1.0% but will generally offer a balance of aggregate reduction and protein product recovery when used at concentrations ranging from 0.01 to 0.10%, and particularly 0.02 to 0.06% or 0.02% to 0.05%.

Soluble multivalent anions of mixed chemical character used to practice certain embodiments may include organic molecules with at least one negative charge and additional features that confer a mixed chemical character such as moieties providing the ability to participate in hydrogen bonding, hydrophobic interactions, pi-pi bonding, metal coordination, and intercalation. Examples of multivalent anions embodying these characteristics include heptanoic acid, octanoic acid, octenoic acid, nonanoic acid, nonenoic acid, decanoic acid, polyaspartic acid, and numerous other organic acids. Such agents may be applied at concentrations ranging from about 0.005% to about 5% but will generally offer a beneficial balance of aggregate reduction and protein product recovery when used at concentrations ranging from about 0.05 to about 1%, and particularly about 0.2% to about 0.5%.

In certain embodiments, the aggregate reducing performance of the method and/or the recovery of the desired protein may be enhanced by the co-addition of soluble organic agents that independently lack sufficient chemical influence to achieve the same level of aggregate reduction as other embodiments. Examples of such additional agents may include but are not limited to nonionic or zwitterionic surfactants such as Tween, Triton, Brij, CHAPS, CHAPSO, and octyl glucoside; organic polymers such as polyethylene glycol (PEG), polypropylene glycol, and polyvinyl pyrrolidone, and generally having a molecular weight less than 1000 Daltons; organic solvents such as ethylene glycol, propylene glycol, dimethyl sulfoxide, ethanol, propanol, isopropanol, phenoxyethanol; carbohydrates; and ureides including urea, hydantoin, and allantoin. Examples may also include soluble non-multivalent cation agents that are added for another purpose, such as but not limited to the inactivation of virus, including benzalkonium chloride, methylene blue, and tri(n-butyl)phosphate, among others. Examples in certain embodiments include ureides in supersaturating amounts, such as uric acid in amounts greater than 0.0025%, and allantoin in amounts greater than 0.56%.

In certain embodiments, the multivalent ions and particles of mixed chemical character must be present together for a period sufficient to accomplish aggregate reduction. They may be added together, or the soluble agent added in advance for an indeterminate period. In some embodiments, advance addition of the multivalent ions may produce better results, but the other format will produce adequate results for many applications. The time required to practice the methods disclosed herein will depend directly on the concentration of the multivalent cations, the proportion of particles, and to a lesser extent the aggregate content of the protein preparation.

In certain embodiments, methods provide method steps of preparing the sample for addition of the soluble and solid agents of mixed chemical character of the first and second components. The conditions should be of a nature to prevent substantial loss of the protein of interest through interactions with either the multivalent ions or particles. Such conditions will include a conductivity value sufficiently high to suspend strong charge interactions between the protein of interest and multivalent ions or the particles, and may include other additives to modulate other types of chemical interactions.

In certain embodiments, methods disclosed herein unexpectedly provide effective aggregate reduction and removal of soluble agents at substantially elevated conductivity (salt concentration). Charged particles are particularly known for the dependency of their performance on aqueous environments of low conductivity, typically below 10 mS/cm, and most often below 5 mS/cm. These values equate roughly to 100 mM NaCl, and 50 mM NaCl, respectively. In certain embodiments, the methods disclosed herein support effective aggregate reduction and removal of soluble agents at conductivity values of 20-30 mS, frequently up to 40 mS/cm, and sometimes up to 100 mS/cm, or more. In certain embodiments, dissociation of hetero-aggregates increases at higher salt concentrations.

In certain embodiments, methods provide the removal of sample components with the potential to foul chromatography columns used in subsequent purification methods. For example, IgG antibodies are very often purified by affinity chromatography with immobilized protein A. While effective, the chromatography media used to practice this method is extremely expensive and its useful cycle-life may be significantly reduced by application of crude samples. In certain embodiments, samples treated by methods disclosed herein are optically clear and devoid of suspended debris that might impair the function of protein A or other chromatography media. In certain embodiments, purification of a sample according to a methods disclosed herein will increase the IgG binding capacity of protein A by up to 10% or more, and offer a similarly beneficial effect on other capture or subsequent chromatography methods. In certain embodiments, use of the methods disclosed herein will permit protein A to reduce contaminating host protein content by a factor of 10 to 100 or more.

In certain embodiments, methods are provided which may enable subsequent purification methods that otherwise would be impaired by sample components even to the point of being impractical for initial antibody capture from unpurified sources. Host cell DNA, for example, binds more strongly to anion exchangers and hydroxyapatite media than IgG or IgM antibodies. This reduces both their antibody binding capacities and purification performance and impairs their suitability as initial capture methods. In certain embodiments, the methods disclosed herein promote the removal of the majority of DNA before applying sample to these subsequent methods rendering both anion exchangers and hydroxyapatite media practical tools for initial antibody capture/purification.

In certain embodiments, in preparation for using the methods disclosed herein, it is advisable to evaluate the composition of the sample to be treated. The first major variable is the aggregate content of the sample. This can be determined easily using analysis by size exclusion chromatography, and particularly by monitoring the fractionation by simultaneous monitoring at wavelengths of 254-260 nm and 280 nm. This method is also convenient for detection of hetero-aggregates comprising antibody-DNA complexes, even when their hydrodynamic size closely approximates purified antibody. Samples that contain high aggregate levels, or contain aggregates that manifest a 254/280 ratio of 0.5 or greater, or contain antibody-DNA hetero-aggregates with elevated 254/280 ratios are favorable candidates for treatment of the sample with soluble agents of mixed chemical character, such as but not limited to ethacridine and/or methylene blue, to promote dissociation of aggregates before exposing the sample to the surfaces of mixed chemical character. The term "high aggregate levels" is understood to be relative since it will depend on where in an overall purification process the sample derives from. "High" aggregate levels in cell culture supernatant may be up to 50% or more compared to the antibody, whereas "high" aggregate levels after initial purification might include anything over 5%, or even less.

In certain embodiments, it will also be advisable to evaluate the native chemical character of the protein to be purified. IgG antibodies tend to be of electro-neutral-to-alkaline character, with weak or no tendency to bind electropositive surfaces but mild-to-moderate tendency to bind electronegative surfaces. IgM antibodies range from alkaline to acidic in character, generally with a strong tendency to bind electropositive surfaces, and with mild to moderate tendency to bind electronegative surfaces. Practical determination of an antibody's surface character can be accomplished by a pair of simple experiments in which the antibody is applied to a cation exchanger at pH 7.0 and eluted with a linear salt gradient, and applied to and eluted from an anion exchanger under the same conditions. The salt concentration at which the antibody elutes from each exchanger provides a convenient index of the antibody's relative tendencies to bind electronegative or electropositive surfaces, and the salt concentrations required to control such interactions. Such characterization can be performed at multiple pH values to obtain a more complete understanding of the charge characteristics of a particular protein of interest.

In certain embodiments, it will be desirable to select one or more multivalent cations of mixed chemical character. Experimental data reveal that as a general matter, the less hydrophobic the multivalent cation, the higher the recovery of the protein of interest. Also, the less hydrophobic, the wider and higher the concentration range over which the multivalent cation can be applied without significant loss of the desired protein. Thus weakly hydrophobic PEI may be considered a better candidate than the more hydrophobic ethacridine, or the much more hydrophobic chlorhexidine. However, other issues may also need to be taken into consideration in addition to product recovery. PEI embodies well-known cytotoxic properties, and it is difficult to detect with adequate sensitivity to easily validate its removal from a sample through the course of a purification, process. Ethacridine may be useful because of its long history in the field of plasma protein fractionation and as an antiviral agent. In addition, its bright yellow color and intrinsic fluorescence facilitate sensitive measurement of its content in a given sample, thereby aiding documentation of its removal subsequent to practicing the method. Besides that, different multivalent cations may embody different secondary chemical functionalities that bear on their ability to mediate the desired effect. PEI for example is understood to bind DNA chiefly through electrostatic interactions and hydrogen bonding. Ethacridine offers fewer opportunities for both interactions but is known to intercalate DNA. Experimental results demonstrate that it also generally supports more effective aggregate reduction.

In certain embodiments, agents such as ethacridine, methylene blue, chlorhexidine, and polyethyleneimine may be effectively applied at concentrations ranging from less than 0.001% to 1%, depending on the characteristics of the antibody and the composition of the sample. The lowest effective concentrations may be beneficial in most cases because high concentrations can increase the amount of electronegative solids of mixed chemical character required to remove the soluble agents. Experimental data reveal concentrations of 0.01 to 0.1% to fulfill this ideal, and particularly concentrations ranging from 0.02 to 0.06% or 0.02% to 0.05%. The most effective agent and working concentration can be identified and customized for each specific case. It will be apparent to the person of ordinary skill that certain of the above-mentioned agents are known for their ability to inactivate virus, and will have the additional benefit of augmenting the removal of DNA and endotoxins. More than one species of multivalent cation may be employed. Pre-treatment of the sample with multivalent cations may increase the ability of the methods disclosed herein to achieve low aggregate levels in some embodiments.

In certain embodiments, it may be advisable to evaluate solid electropositive and/or electronegative substrates of various character to accommodate the characteristics of the desired protein and the feed stream in which it resides. For example, in some cases an electropositive material having quaternary amine functional groups may have lesser ability to reduce aggregates and/or other contaminants, but support higher recovery of the desired protein, while an electropositive material in the form of TREN may support the opposite results. In some cases an electropositive surface that is useful for one desired protein, may be judged inferior for another. For example, TREN may be useful for IgG antibodies, while a quaternary amine may be better for IgM. The density of the ligands on a substrate may also influence the performance of certain embodiments such as through secondary interactions between sample component and the chemical surface(s). For example, experimental data document that in certain embodiments, substrates having a high density of TREN may outperform substrates having a low-density of TREN.

In certain embodiments, it may be convenient to begin with an equally balanced mixture of particles of mixed chemical character, at a combined volumetric ratio of 5% solids to sample. Through the course of optimizing the system to accommodate the needs of a particular sample, the ratio of solids to sample volume may be reduced to identify the effectivity threshold for that particular sample/treatment system. The ratio of electronegative to electropositive functionalities may also be varied, as may be the choice of secondary chemical functionalities included on the surface(s). The experimental workload to evaluate these variations can be substantially reduced by applying statistically based Design of Experiments (so-called DoE). Convenient particles of mixed chemical character may include commercial anion exchangers and cation exchangers, chelating resins, hydrophobic resins, and products marketed to perform so-called mixed-mode chromatography.

In certain embodiments, initial conditions for evaluation should be performed at pH and conductivity values that prevent antibody loss through binding to the various surfaces, but beyond that, experiments should specifically evaluate higher conductivity levels since they may support enhanced dissociation of aggregates and/or antibody-contaminant complexes. As a matter of convenience, initial experiments with IgG antibodies can be conducted at a pH of 6.5-7.5 and a conductivity of about 10 to about 15 mS/cm. Initial experiments with IgM antibodies can be conducted at the same pH but a conductivity of 20-30 mS/cm. Subsequent experiments with each can be performed with higher and lower conductivities, and/or higher or lower pH values to identify the conditions that support a complementary combination of aggregate reduction and antibody recovery. Although it is not a primary object of the methods disclosed herein to reduce levels of host cell protein contaminants, it may offer a significant contribution in this regard, in particular with respect to the content of highly alkaline and/or highly acidic host contaminants.

In certain embodiments, the period of time which the soluble and solid agents of mixed chemical character should be present can be determined by simple experiments, in which samples are analyzed by SEC over a time course, for example every 10 minutes for 1 hour, or other increments and durations as indicated by data from the examples as described below.

It will be apparent to the person of ordinary skill in the art that, in addition to reducing the content of homoaggregates and hetero-aggregates, certain embodiments may also substantially reduce the content of host cell protein, host cell DNA, endotoxin, and virus.

In certain embodiments, the solid materials of the first and second components may be cleaned and recycled after use. In other embodiments, they may be discarded after use.

In certain embodiments, a methods disclosed herein may be practiced prior to other chromatography steps, where this practice has the dual benefit of protecting the chromatography media from fouling by cell culture media components, and improving the quality of purification by virtue of having put the target product in a more homogeneous state than it was in the untreated sample.

In certain embodiments, methods may provide for the use of electrostatically charged and/or electrostatically neutral particles mixed and enclosed by neutral materials, embedded in neutral materials, or enclosed by or embedded in materials that bear the same charge as the electrostatically charged particles. In certain embodiments, the electronegative and/or electropositive surface may comprise additional chemical functionalities, including but not limited to the ability to participate in hydrophobic interactions, pi-pi bonding, hydrogen bonding, and metal affinity.

In certain embodiments, a protein preparation treated by the disclosed method may be further treated to reduce aggregate content.

Additional objects and advantages of the methods disclosed herein will be set forth in part in the description which follows, and in part will be obvious from the description, or may be learned by practice of the methods. The objects and advantages of the methods disclosed herein will be realized and attained by means of the elements and combinations specified in the claims.

It is to be understood that both the foregoing general description and the following detailed description are exemplary and explanatory only and are not restrictive of the methods, as claimed.

EXAMPLES

The following examples illustrate prototypes demonstrating the efficacy of certain embodiments.

Example 1

1 L of cell culture harvest containing about 1 g/L of an IgG monoclonal antibody specific for HER2 antigen was treated with 1% allantoin. Conductivity was about 13 mS/cm and pH was about 6.8. The additives had the effect of accelerating sedimentation. Solid materials were removed by filtration, leaving a sparking clear antibody-containing filtrate. Antibody recovery was 99%. 20 mL of BioWorks TREN hi-sub, an agarose porous particle-based electropositive metal affinity material was packed in a column (1.6×10 cm) and equilibrated to 50 mM Hepes, 150 mM NaCl, pH 7.0. The clarified filtrate was passed through the column at a linear flow rate of 200 cm/hr. The original harvest contained more than 20% aggregates, particularly containing at least 10% so-called high molecular weight aggregates. The treated sample contained less than 0.05% high molecular weight aggregates and less than 4% total aggregates. DNA as measure by fluorescent dye assay was reduced by greater than 98%, but qPCR indicated that reduction was actually greater than 99.999%. Histone proteins were reduced by at least 98% and general host protein levels, as measured by Cygnus ELISA was reduced by 62%. Antibody recover was 99%.

Example 2

The procedure of Example 1 was repeated except substituting TREN for a 1:1 mixture of TREN plus Dowex AG1x2, a hydrophobic electropositive particulate material. All results were nominally the same, except that antibody recovery was reduced to 95% and analytical size exclusion chromatography showed that two strongly hydrophobic contaminants evident after. Example 1, were eliminated.

Example 3

The procedure of Example 2 was repeated except that cell-containing harvest was treated with 0.05% octanoic acid in addition to 1% allantoin. Host protein contamination was reduced by more than 70%, and antibody recovery was reduced to 90%. Octanoic acid was undetectable in the treated sample, appearing to indicate that it was bound to the solid material(s). Aggregates were reduced to less than 3%. DNA and histone content were reduced by 99%.

Example 4

The procedure of Example 2 was repeated with an IgM monoclonal antibody, except that NaCl was added to the cell-containing harvest to a concentration giving a conductivity of 20 mS/cm and the pH was adjusted to 6.0. The aggregate content of the untreated harvest was greater than 30%. The column was equilibrated to 50 mM MES, 200 mM NaCl, pH 6.0. 99% of the DNA and histones were removed, along with all high molecular weight aggregates. Total aggregate content was reduced to about 2%. Antibody recovery was 84%. Total host protein was reduced 67%. The experiment was repeated at a conductivity throughout of 25 mS/cm, corresponding to the addition of a 50 mM increment of sodium chloride over and above the concentration added to achieve a conductivity of 20 mS/cm. Antibody recovery increased to 98% and all other measures remained the same. The experiment was repeated at a conductivity of 40 mS/cm. Host protein reduction diminished to about 47%, but all other performance measures remained unchanged.

Example 5

The procedure of Example 3 was repeated except substituting 0.025% ethacridine for octanoic acid, and using a column packed with acrylate-based porous particles bearing the metal affinity ligand iminodiacetic acid (Profinity, Bio-Rad) and styrene divinylbenzene particles (Chelex 100, Bio-Rad) in a 1:1 mixture. The treated sample was free of yellow color, while the chromatography media was intensely yellow, indicating removal of the ethacridine. DNA, histones, and nucleosomes were reduced by 99%, while antibody recovery was 99%. High molecular weight aggregates were completely eliminated, while total aggregates were reduced to less than 2%. Analytical SEC also demonstrated the removal of strongly hydrophobic contaminants. Total host protein contamination was reduced 63%.

Example 6

The form of Example 5 was repeated except including negatively charged hydrophobic interaction particles (Macroprep T-butyl, Bio-Rad) mixed in a 1:1:1 ratio with the Profinity and Chelex. The treated sample was free of yellow color, while the chromatography media was intensely yellow, indicating removal of the ethacridine. DNA, histones, and nucleosomes were reduced by 99%, while antibody recovery was 99%. High molecular weight aggregates were completely eliminated, while total aggregates were reduced to less than 2%. Analytical SEC also demonstrated the removal of strongly hydrophobic contaminants. Total host protein contamination was reduced 64%.

Example 7

Dynamic binding experiments were conducted on immobilized protein A (rAF protein A Toyopearl 650M, Tosoh), comparing the harvest clarified by centrifugation and microfiltration versus the treatment of Example 2. Dynamic binding capacity on the microfiltered material was 28 mg/mL. Dynamic binding capacity on the material from Example 3 was 35 mg/mL. Host protein content of the microfiltered material after protein A purification was 792 parts per million. Host protein content of the Example 3-treated material was less than 1 part per million. Thus practicing the disclosed method increased IgG binding capacity by about 20% and IgG purity by nearly 800-fold.

Example 8

The procedure of Example 2 was reproduced except increasing the operating pH to 8.0 and reducing the conductivity of the cell culture supernatant to 4.7 by dilution of the sample with 2 parts water and reformulating the buffer to contain 50 mM Tris, 50 mM NaCl, pH 8.0. Performance was nominally the same as Example 2 except that general host protein removal was 83%.

Example 9

The procedure of Example 2 was reproduced except increasing the overall proportion of particles from 2% to 5%. Results were nominally unchanged except that antibody recovery was reduced to 84%. In subsequent experiments where the proportion of total particles was 2%, and the proportion represented by Dowex AG1x2 was reduced to 25%, and 12.5% of the TREN content, respectively, antibody recovery increased to 97 and 98% respectively. Removal of the hydrophobic contaminants was still effective at the reduced Dowex levels. All other results were nominally equivalent to Example 2.

Example 10

The form of example 1 was repeated except reducing the conductivity of the sample to about 5 by dilution with 2 parts water. The proportion of aggregates of all sizes roughly doubled.

Example 11

The procedure of Example 2 was repeated except replacing Dowex AG1x2 with UNOsphere Q. UNOsphere Q more effectively removed residual ethacridine. Results were otherwise similar.

Example 12

The procedure of Example 3 was repeated except increasing caprylic acid to 0.4%, reducing the operating pH to 5.2, and incubating for 2 hours before addition of TREN particles, then incubating for 4 hours before removing the solids. Aggregate content was reduced to less than 0.1%. Host protein was reduced 99.9%.

Example 13

The materials and conditions of Example 12, except for an operating pH of 5.6, were applied to a cell culture harvest containing and IgM monoclonal antibody. Aggregates were reduced from an original 22% compared to the non-aggregated antibody, to less than 0.1%. Host proteins were reduced by more than 98%.

Example 14

An IgG-containing cell culture harvest containing 259,218 ppm host protein contaminants and 21% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 308 ppm and aggregates to less than 0.05%.

Example 15

An IgG-containing cell culture harvest containing 243,997 ppm host protein contaminants and 24% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 305 ppm and aggregates to less than 0.05%.

Example 16

An IgG-containing cell culture harvest containing 243,997 ppm host protein contaminants and 24% aggregates was conditioned by addition of 1% allantoin, 0.4% caprylic acid, pH 5.6; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 3,551 ppm and aggregates to less than 0.5%.

Example 17

An IgG-containing cell culture harvest containing 319,230 ppm host protein contaminants and 22% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 237 ppm and aggregates to less than 0.01%. The sample was loaded onto a multimodal hydrophobic cation exchanger (Millipore, HCX) at pH 7.0, and eluted in an increasing NaCl gradient. Host protein contamination was reduced to 37 ppm. The sample was loaded onto a multimodal hydrophobic anion exchanger at 1 M NaCl (Capto adhere, GE Healthcare) and eluted with a decreasing NaCl gradient, reducing host protein contamination to 1 ppm. Alternatively, the post-HCX sample was loaded onto a column of UNOsphere Q (Bio-Rad laboratories) equilibrated to 50 mM Tris, pH 8.0, operated in void exclusion mode, reducing host protein contamination to an undetectable level.

Example 18

An IgG-containing cell culture harvest containing 287,621 ppm host protein contaminants and 19% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 510 ppm and aggregates to less than 0.1%. Conditioned harvest was loaded onto a cation exchanger (UNOsphere HRS and eluted in an increasing NaCl gradient. Host protein contamination was reduced to less than 1 ppm, but aggregates increased to slightly more than 0.2%. The sample was subsequently fractionated on a column of hydroxyapatite (CHT Type I, 40 micron), eluted in a phosphate gradient, reducing aggregates to less than 0.01%, and host proteins to a an undetectable level.

Example 19

An IgG-containing cell culture harvest containing 206,994 ppm host protein contaminants and 18% aggregates was loaded onto a protein A column (Toso BioScience), washed with 50 mM sodium phosphate, 150 mM NaCl, pH 7.2, then eluted with 100 mM acetic acid. Host protein was reduced to 1,917 ppm, and aggregates to 1.8%. In a parallel experiment with all details the same except that the column was washed with 50 mM phosphate, 1.0 M NaCl, pH 7.2, host protein was reduced to 527 ppm, and aggregates to 1.6%. Another IgG-containing cell culture harvest containing 287,661 ppm host protein contaminants and 19% aggregates was loaded onto a protein A column (Toso BioScience), washed with 50 mM sodium phosphate, 150 mM NaCl, pH 7.2, then eluted with 100 mM acetic acid, reducing host protein contamination to 1,337 ppm, and aggregates to 2.1%.

Example 20

An IgG-containing cell culture harvest containing 287,621 ppm host protein contaminants and 19% aggregates was split into two portions. The first portion was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 167 ppm and aggregates to less than 0.01%. Conditioned harvest was loaded onto a protein A column (Toso BioScience), washed with 50 mM sodium phosphate, 150 mM NaCl, pH 7.2, then eluted with 100 mM acetic acid. Host protein was reduced to an undetectable level. In a parallel experiment with all details the same except that the column was washed with 50 mM phosphate, 1.0 M NaCl, pH 7.2, host protein was also reduced to an undetectable level. The second portion was conditioned by addition of 1% allantoin and 0.025% ethacridine; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 2,985 ppm and aggregates to less than 0.1%. Conditioned harvest was loaded onto a protein A column (Toso BioScience), washed with 50 mM sodium phosphate, 150 mM NaCl, pH 7.2, then eluted with 100 mM acetic acid. Host protein was reduced to 1 ppm. In a parallel experiment with all details the same except that the column was washed with 50 mM phosphate, 1.0 M NaCl, pH 7.2, host protein was also reduced to 1 ppm.

Example 21

An IgG-containing cell culture harvest containing 251,852 ppm host protein contaminants and 18% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 131 ppm and aggregates to less than 0.01%. Application of the sample to Capto adhere reduced host protein to 3 ppm. Application of the sample to Capto adhere ImpRes reduced host protein to 1 pm.

Example 22

An IgG-containing cell culture harvest containing 191,180 ppm host protein contaminants and 16% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed by microfiltration on a 0.45 micron membrane, reducing host proteins to 2,063 ppm, and aggregates to 1.2%. The sample was then passed through an electropositive depth filter (Sartorius PC1), reducing host proteins to 196 ppm and aggregates to less than 0.01%. Application of the sample to a column of UNOsphere Q operated in void exclusion mode reduced host proteins to 1 ppm. Alternatively, application of the sample to a column of Nuvia Q operated in void exclusion mode reduced host proteins to 1 ppm. In a parallel series of experiments with all details the same except substituting 0.2% capric acid in place of 0.4% caprylic acid, host protein was reduced to 1,920 ppm after membrane filtration, reduced to 132 ppm after depth filtration, and to less than 1 ppm after both of the anion exchange steps.

Example 23

An IgG-containing cell culture harvest containing 176,244 ppm host protein contaminants and 14% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed by microfiltration on a 0.45 micron membrane, reducing host proteins to 2,063 ppm, and aggregates to 1.2%. The sample was then passed through an electropositive depth filter (Sartorius PC1), reducing host proteins to 196 ppm and aggregates to less than 0.01%. Application of the sample to a column of UNOsphere Q operated in void exclusion mode reduced host proteins to 1 ppm. Alternatively, application of the sample to a column of Nuvia Q operated in void exclusion mode reduced host proteins to 1 ppm. In a parallel series of experiments with all details the same except substituting 0.2% capric acid in place of 0.4% caprylic acid, host protein was reduced to 1,920 ppm after membrane filtration, reduced to 132 ppm after depth filtration, and to less than 1 ppm after both of the anion exchange steps.

Example 24

An IgG-containing cell culture harvest containing 243,997 ppm host protein contaminants and 24% aggregates was conditioned by addition of 1% allantoin, 0.4% caprylic acid, pH 5.6; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 3,551 ppm and aggregates to less than 0.5%. Ammonium sulphate precipitation reduced host protein content to 1,423 ppm and aggregates to less than 0.1%. A subsequent anion exchange chromatography step on a QA monolith reduced host protein to 2 ppm. Ammonium sulphate precipitation performed on harvest that was clarified by centrifugation and microfiltration reduced host protein to 30,114 ppm. Anion exchange reduced it further to 411 ppm. These results show that the benefits of chromatin removal apply also to precipitation methods, and also show that the benefits ripple past the first step to a later chromatography step.

Example 25

An IgG-containing cell culture harvest containing 256,482 ppm host protein contaminants and aggregates was conditioned by addition of electropositive metal affinity particles (TREN 40 high, Bio-Works) were added in an amount of 4%, and incubated mixing for 4 hours, then solids were removed through an electropositive depth filter (Sartorius PC1). Host proteins were reduced to 1,183 ppm and aggregates to less than 0.4%. Application of the sample to Capto adhere reduced host protein to 147 ppm and aggregates to less than 0.05%. A follow-on anion exchange chromatography step on UNOsphere Q operated in void exclusion mode reduced host protein to 3 ppm.

It will be apparent to persons skilled in the art, given the wide diversity of cells, cell culture formulations, product characteristics and expression levels, and relative cell mortality at harvest, that accommodate any given protein produced in any given cell culture medium, and harvested within a particular range of cell mortalities will require that the specific types of particles, their relative volumes, and the specific conditions will need to be developed experimentally on an individual basis. It will be further apparent, based on the examples and guidelines provided herein, that there may be some trial and error to identify an optimal combination of materials and conditions is within the purview of a person of ordinary skill in the art.

After use, all solid materials may optionally be discarded or regenerated in accordance with standard techniques known to those skilled in the art.

The present embodiments may be combined with various purification methods to achieve the desired levels of purification. Examples include, but are not limited to, other methods commonly used for purification of antibodies, such as protein A and other forms of affinity chromatography, anion exchange chromatography, cation exchange chromatography, hydrophobic interaction chromatography, immobilized metal affinity chromatography, and additional mixed mode chromatography methods. It is within the purview of a person of ordinary skill in the art to develop appropriate conditions for the various methods and integrate them with the methods herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present embodiments.

Many modifications and variations of the methods disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the methods being indicated by the following claims.

What is claimed is:

1. A method of reducing aggregate and product-contaminant complex content in a protein preparation comprising an antibody, the method comprising: (a) contacting the preparation with allantoin at a concentration in a range from 0.6% to 50% (w/v), wherein after the contacting of (a), the preparation is supersaturated with the allantoin, (b) contacting the protein preparation with at least a first solid surface comprising a first surface-bound ligand selected from tris (2-aminoethyl)amine (TREN), diethylenetriamine, triethylenetetramine, tetraethylenepentamine, polypropylenimine tetraamine, deferoxamine (desferrioxamine), histidine, histamine, polyhistidine, arginine, polyarginine, lysine, polylysine, and polyallylamine, wherein operating conditions are selected to prevent binding of the antibody to the first solid surface; and (c) separating the protein preparation from the first solid surface; wherein when more than one surface-bound ligand is present, each surface-bound ligand is independently either of the same net charge or charge neutral.

2. The method of claim 1, wherein the first surface-bound ligand provides further chemical functionality selected from the group consisting of electrostatic interactions, hydrophobic interactions, pi-pi interactions, hydrogen bonding, and combinations thereof.

3. The method of claim 1, wherein the contacting step further comprises contacting the protein preparation with at least a second surface-bound ligand that provides a chemical functionality that does not bind a metal.

4. The method of claim 3, wherein the first solid surface comprises the second surface-bound ligand.

5. The method of claim 3, wherein a second solid surface comprises the second surface-bound ligand and the second solid surface does not substantially interact with the antibody.

6. The method of claim 3, wherein the chemical functionality that does not bind a metal provides a chemical functionality selected from the group consisting of metal affinity, electrostatic interactions, hydrophobic interactions, pi-pi binding, hydrogen bonding, and combinations thereof.

7. The method of claim 1, wherein the net charge on the first surface-bound ligand is positive.

8. The method of claim 7, wherein the first surface-bound ligand is selected from the group consisting of tris(2-aminoethyl)amine (TREN), diethylenetriamine, triethylenetetramine, tetraethylenepentamine, and polypropylenimine tetraamine.

9. The method of claim 1, wherein the concentration of allantoin is selected from the group consisting of (a) from about 0.6 to about 1%; (b) from about 1 to about 2%; and (c) from about 2 to about 5%.

10. The method of claim 1, wherein a conductivity of the protein preparation comprises a range of from about 0.1 mS/cm to about 40 mS/cm, or from about 40 mS/cm to about 200 mS/cm.

11. The method of claim 1, wherein the selected operating conditions comprise a conductivity greater than 20 mS/cm.

12. The method of claim 1, wherein the selected operating conditions comprise a pH in a range of about 5 to about 9.

13. The method of claim 1, wherein the first solid surface comprises a particle or a composite of particles, a fiber or composite of fibers, a membrane or composite of membranes or a monolith or composite of monoliths.

14. The method of claim 1, wherein the contacting further comprises contacting the protein preparation with two or more solid surfaces that are (i) structurally similar to, but distinct from the first solid surface, or (ii) structurally distinct from the first solid surface, and wherein each of the two or more solid surfaces comprise one or more surface-bound ligands different from the first surface-bound ligand.

15. The method of claim 1, wherein the protein preparation comprises a recombinant antibody.

16. The method of claim 1, wherein after (c) the protein preparation has a reduced aggregate content, wherein the aggregate content is reduced by an amount in a range selected from the group consisting of (a) from about 50% to about 99%; (b) from about 25% to about 50%; (c) from about 10% to about 25%; (d) from about 5% to about 10%; (e) from about 1% to about 5%; and (f) from about 0.1% to about 1%.

17. The method of claim 1, further comprising, before (c), contacting the protein preparation with at least one organic additive to reduce aggregate contaminants in the preparation, wherein the organic additive is selected from the group consisting of an electropositive ion, an electronegative ion, an organic solvent, an organic polymer, and a surfactant.

* * * * *